United States Patent [19]

McGuire et al.

[11] Patent Number: 5,718,955
[45] Date of Patent: Feb. 17, 1998

[54] COMPOSITE FOR CONTROLLING OXYGEN FLUX INTO THERMAL CELLS

[75] Inventors: Kenneth S. McGuire; Peter W. Hamilton, both of Cincinnati, Ohio

[73] Assignee: The Procter & Gamble Company, Cincinnati, Ohio

[21] Appl. No.: 614,036

[22] Filed: Mar. 12, 1996

[51] Int. Cl.⁶ .................................................. B01D 67/06
[52] U.S. Cl. ............................ 428/35.7; 126/204; 55/320
[58] Field of Search ....................... 428/35.7; 126/204; 55/320

[56] References Cited

U.S. PATENT DOCUMENTS

| | | | |
|---|---|---|---|
| 3,754,375 | 8/1973 | Bouchilloux et al. | 55/16 |
| 4,230,463 | 10/1980 | Henis et al. | 55/16 |
| 4,243,701 | 1/1981 | Riley et al. | 427/244 |
| 4,410,568 | 10/1983 | Iwama et al. | 427/244 |
| 4,590,098 | 5/1986 | Kazuse et al. | 427/244 |
| 4,666,644 | 5/1987 | Watson | 264/41 |
| 4,871,378 | 10/1989 | Pinnau | 55/16 |
| 4,881,954 | 11/1989 | Bikson et al. | 55/16 |
| 5,046,479 | 9/1991 | Usui | 126/204 |
| 5,102,552 | 4/1992 | Callahan et al. | 210/654 |

FOREIGN PATENT DOCUMENTS

| | | |
|---|---|---|
| 0638300A1 | 2/1995 | European Pat. Off. |
| 0686383A1 | 12/1995 | European Pat. Off. |

OTHER PUBLICATIONS

"Coating Processes" from vol. 6 of Encyclopedia of Chemical Technology, fourth edition, pp. 606-635.

Primary Examiner—Charles Nold
Attorney, Agent, or Firm—Ronald W. Kock

[57] ABSTRACT

A composite material for controlling oxygen flux into a thermal cell comprises a bottom sheet formed to have a pocket. The bottom sheet is impermeable to oxygen. A plurality of particles is placed in the pocket. The plurality of particles reacts exothermally when exposed to oxygen. A top sheet is sealed to the bottom sheet at a flange around the pocket to enclose the plurality of particles such that the particles cannot fall out of the pocket. The top sheet has a substrate which is highly permeable to oxygen. The substrate is coated with an oxygen permeable silicone based elastomer to a thickness which regulates an oxygen flux into the pocket when the top sheet is exposed to oxygen. The composite material further comprises an oxygen impermeable barrier film bonded to the top sheet by pressure sensitive adhesive for preventing exposure of the top sheet to oxygen until the body warmer is intended to be used. A method for making a top sheet material involves coating a silicone rubber layer onto a smooth surface, partially curing the silicone, pressing a porous substrate against the silicone rubber layer, and completely curing the silicone rubber such that it adheres to the substrate.

14 Claims, 1 Drawing Sheet

5,718,955

COMPOSITE FOR CONTROLLING OXYGEN FLUX INTO THERMAL CELLS

FIELD OF THE INVENTION

The present invention relates to oxygen permeable materials, and more particularly to such materials wherein material thickness is used to control oxygen flux from ambient air into a thermal cell.

BACKGROUND OF THE INVENTION

Thermal cells for body warmers are well known in the art, particularly those which use a reactive iron powder and activated carbon mixture. Such cells require oxygen to produce a controlled exothermic reaction which provides heat over several hours. Typically, the mixture is packaged in an air permeable pocket, which is sealed in an impermeable outer pouch until ready for use. The permeable pocket may be a nonwoven material or a perforated material. In either case, mixture particles may migrate through perforations or between filaments of nonwoven when the assembly is jostled. Inadvertent leakage of mixture, particularly carbon, may contaminate a users clothing and reduce performance of the thermal cell.

In a typical body warmer, more than one thermal cell may be present. Placing smaller cells side-by-side with some substrate material between them enables the body warmer to have more flexibility to conform to body contours than a single cell can provide. The smaller the heat cell, the more critical the location and number of perforations or consistency of nonwoven substrate placed over the cells, in order to control oxygen flux to the cells. Such control is required to insure that cells do not overheat and possibly burn the user or run out of heating potential too soon.

Gas permeable membranes have been available for separation processes. For example, U.S. Pat. No. 5,102,552 to Callahan et al., issued Apr. 7, 1992, discloses a UV curable polymer coated onto a microporous support having an average pore size from about 0.005 microns to about 0.2 microns. U.S. Pat. No. 3,754,375 to Bouchilloux et al., issued Aug. 28, 1973, discloses an "anisotropic membrane having excellent mechanical properties combined with good permeation characteristics. It comprises a vinyitriorganosilane polymer or copolymer" having a dense layer of 0.01 to 10 micron average thickness and a porous layer 20% to 80% open area.

Others have even applied gas permeable membranes to heat cells, but with limited success. For example, U.S. Pat. No. 5,046,479 to Usui, issued Sept. 9, 1991, discloses a method of controlling oxygen permeation through a microporous film which is subject to a "heat fusion treatment" intended to restrict oxygen permeability to a disposable body warmer. A flat bag containing iron powder heat generating agent has an air permeable surface having an air permeability per unit of 5000 to 10,000 sec/100 cc. Microporous films, unfortunately, are very expensive.

OBJECTS OF THE INVENTION

It is an object of the present invention to provide an inexpensive composite material having excellent control of oxygen permeability for use with a thermal cell.

It is another object of the present invention to provide a composite material which has no perforations or voids through which particles of thermal mixture can leak from a pocket containing such mixture.

It is a further object of the present invention to provide a composite material which is heat sealable to the flange of an impermeable pocket containing a thermal mixture and from which is easily peelable an impermeable coversheet that seals out oxygen until the thermal cell is ready for use.

It is still another object of the present invention to provide a method for making a composite material having excellent control of oxygen permeability for use with a thermal cell.

SUMMARY OF THE INVENTION

In practicing the present invention, a nonwoven or other porous substrate is silicone coated and forms the top sheet of a thermal cell of a body warmer. The silicone coated substrate is permeable to oxygen at a preferred rate, yet is non-porous to particulate materials within the heat cell. The oxygen permeation rate is easily adjusted by varying the thickness of the silicone coating. The substrate provides structural integrity since thin silicone materials by themselves are known to he easily torn. A barrier film, which is removed to initiate oxygen permeation and heat generation, can he easily peeled from a silicone coating, since silicone coatings act as release surfaces for pressure sensitive adhesives.

In one aspect of the present invention, a composite material for controlling oxygen flux into a thermal cell comprises a bottom sheet formed to have a pocket. The bottom sheet is impermeable to oxygen. A plurality of particles is placed in the pocket. The plurality of particles reacts exothermally when exposed to oxygen. A top sheet is sealed to the bottom sheet at a flange of the pocket to enclose the plurality of particles such that the particles cannot fall out of the pocket. The top sheet has a substrate which is highly permeable to oxygen. The substrate is coated with an oxygen permeable silicone based elastomer to a thickness which regulates an oxygen flux into the pocket when the top sheet is exposed to oxygen.

The composite material further comprises a means for preventing exposure of the top sheet to oxygen until the body warmer is intended to be used. The means may be an oxygen impermeable barrier film bonded to the top sheet by pressure sensitive adhesive. The means may also he an oxygen impermeable pouch into which a body warmer having the thermal cell is placed for storage.

The plurality of particles comprises a reactive iron mixture. The mixture may include activated carbon, water, and salts to increase an exothermic reaction rate when the mixture is exposed to oxygen. The oxygen flux into the pocket is preferably about $1.75 \times 10^5$ cm$^3$/100 in.$^2$/day. The substrate comprises a nonwoven having openings of at least 2 microns, and the silicone based elastomer comprises poly (dimethyl siloxane) printed onto the substrate at a thickness of about 0.0001 inches.

In another aspect of the present invention, a method of making a composite material for controlling oxygen flux into a thermal cell comprises the steps of coating a silicone rubber layer onto a smooth surface and partially curing the silicone rubber layer to enhance its peelability from the smooth surface. Other steps include pressing an oxygen porous substrate against the silicone rubber layer and then completely curing the silicone rubber layer such that it adheres to the oxygen porous substrate. The method has a further step of peeling the oxygen porous substrate and silicone rubber layer from the smooth surface. The smooth surface may he a drum and the oxygen porous substrate may be a continuous web wrapped about a portion of the drum.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
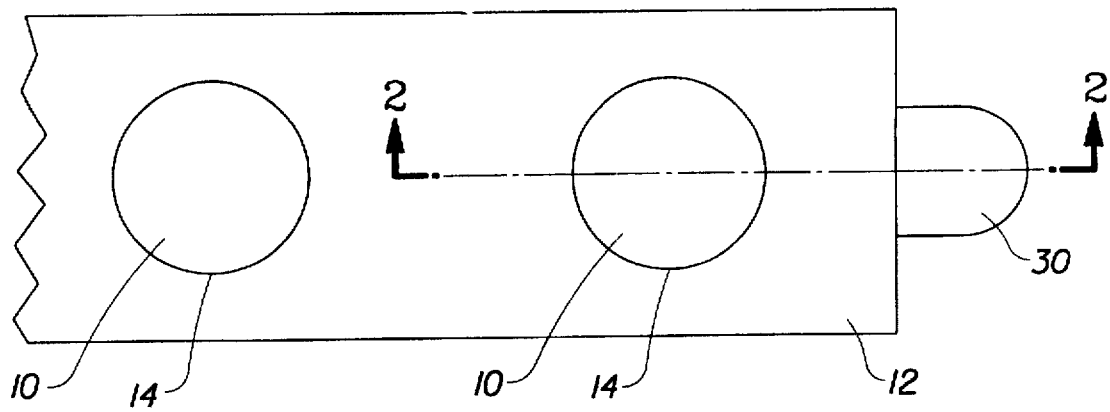
FIG. 1 is a top plan view of a preferred embodiment of a composite material for controlling oxygen flux into a thermal cell of the present invention, disclosing an inverted cylindrical pocket projecting upward from a flange of composite material.
Figure 2:
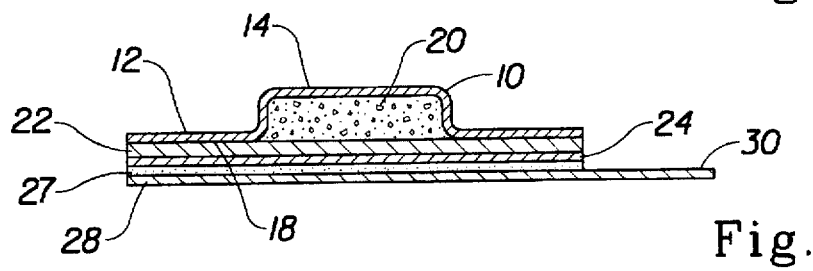
FIG. 2 is a sectioned side elevation view thereof, taken along section line 2—2 of FIG. 1, showing an impermeable peelable barrier film adhesively bonded to the composite material for protecting the thermal mixture from oxygen.
Figure 3:
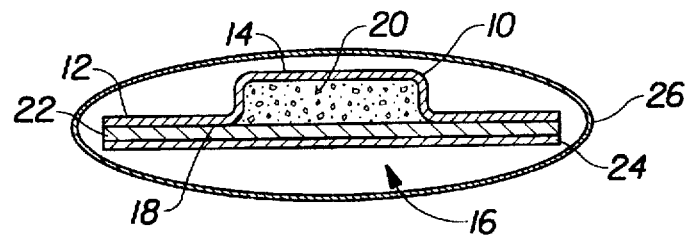
FIG. 3 is a sectional side view thereof, similar to FIG. 2, but showing the layers of the composite material and particles of a thermal mixture in the pocket when the thermal cell is protected from oxygen by being placed in an impermeable pouch.

Referring now to the drawings, and more particularly to FIGS. 1, 2 and 3, there is shown a first preferred embodiment of the present invention, which provides at least one thermal cell 10. Thermal cell 10 has a bottom sheet 12, which is formed into a pocket 14. Bottom sheet 12 is sealed at a flange 18 around pocket 14 to a top sheet, generally being indicated as 16. Closed pocket 14 preferably contains a thermal mixture 20. Top sheet 16 is a composite material comprised of a substrate 22 and a coating silicone rubber 24. Substrate 22 is highly permeable to oxygen.

FIG. 3 shows a sectioned side view of thermal cell 10. In the embodiment of FIG. 3, thermal cell 10 is enclosed in an oxygen impermeable pouch 26. Thermal mixture 20 is activated by opening impermeable pouch 26, thereby causing oxygen to permeate through top sheet 16 and into thermal mixture 20.

FIG. 2 shows a sectioned side view similar to FIG. 3, but with peelable film 28 bonded a pressure sensitive adhesive 27 to silicone rubber coating 24. In this embodiment peelable film 28 has a tear tab 30. When tear tab 30 is used to peel peelable film 28 from silicone robber coating 24, oxygen from air passes through silicone rubber coating 24 and substrate 22 into thermal mixture 20. Pressure sensitive adhesive 27 preferably adheres to peelable film 28 rather than silicone rubber coating 24.

Further details, concerning the intended use of the present invention with a thermal cell of a body warmer, may be found in copending application Ser. No. 08/496,373, entitled "Elastic Back Wrap Having Diamond-shaped Pattern and Anti-slip Means, filed 6/29/95, with obligation to assign that application to the assignee of the present application, and which is hereby incorporated by reference.

In a particularly preferred embodiment of the present invention, substrate 22 is a Durapel 0.65 μm microporous membrane available from Millipore Corporation, of Bedford, Mass. silicone rubber 24 is coated onto substrate 22 by first mixing hydroxy terminated poly(dimethyl siloxane), or PDMS, with a viscosity of approximately 1000 centistokes with a tin octoate catalyst in a mass ratio of 10:0.25. The PDMS mixture is coated onto the microporous membrane with a sharp blade to a thickness of about 0.0001 inches. The PDMS mixture is then exposed to vapors of tetraethoxy silane, or TEOS, for 5 to 15 minutes. Longer exposure times correspond with thicker coatings. Residual, unreacted PDMS is washed away with toluene and then methanol. Oxygen permeation rates vary from $3.5 \times 10^5$ to $1.5 \times 10^5$ cm$^3$/100 in.$^2$/day result for TEOS exposure times from 5 to 15 minutes.

Although microporous membranes provide a very uniform coating surface and uniform pore size, they are considered to be very expensive. By comparison, expensive non-woven materials typically provide a fairly uniform coating surface and a fairly uniform pore size. Inexpensive non-wovens typically have very rough coating surfaces and very large pores, which makes coating a 0.0001 inch thick layer of initially liquid silicone robber onto their surfaces very difficult when using coating techniques known in the art, such as wire wound rod coating and gravure print coating. By coating the liquid silicone rubber onto a smooth surface, bringing the non-woven into contact with the partially cured silicone rubber, and then completely curing the silicone rubber while it is in contact with the non-woven, the silicone rubber can be transferred from the smooth surface to the non-woven. This method results in a uniform coating of silicone rubber on the non-woven's rough surface. It is believed that a preferred coating method, shown in FIG. 4, would automate the coating of a 0.0001 inch thick layer of silicone rubber onto the uneven surface of an inexpensive non-woven web. The method shown in FIG. 4 would of course also be applicable to expensive microporous membranes.

Figure 4:
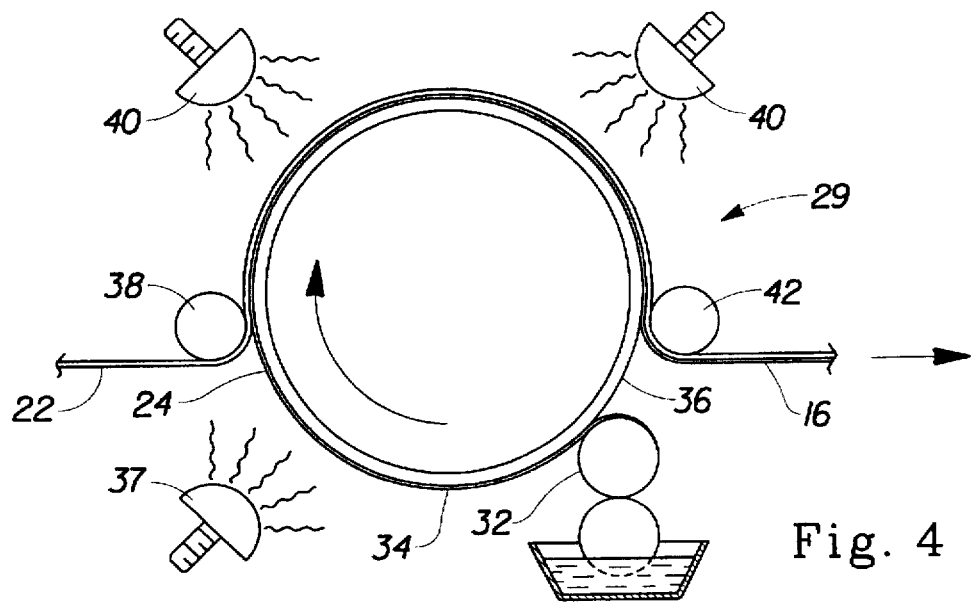
FIG. 4 is a side elevation view of a process for making the composite material for controlling oxygen flux into a thermal cell of the present invention, disclosing a drum, heat lamps, an applicator roll, and a pair of continuous web handling rolls.

FIG. 4 shows a process generally referred to as 29 for making top sheet 16. Silicone rubber application system 32 deposits about 0.0001 inches of uncured, liquid silicone rubber onto drum 36 as drum 36 rotates. The surface of drum 36 is preferably polished smooth. It may be stainless steel, chrome plated material, or other suitable smooth surface. Liquid silicone rubber may be partially cured by initial curing source 37, which is preferably a heating device used to heat cure silicone rubbers. Other curing means, such as ultraviolet light may also be used. Automated process 29 has a web of substrate 22 threaded between infeed idler roll 38 and drum 36. Substrate 22 is preferably a non-woven or microporous film. In this process, liquid silicone rubber 34 is preferably first deposited onto surface of substrate 22. As drum 36 rotates, liquid silicone rubber 34 is partially cured by curing source 37. Curing source 37 is preferably a heater used to cure heat curable silicone rubbers. After liquid silicone rubber 34 is transformed into solid silicone rubber 24, substrate web 22 is pressed against silicone rubber coating 24 by infeed idler roll 38. Tension in substrate web 22 maintains it in contact with silicone rubber coating 24. As drum 36 rotates, silicone rubber coating 24 is completely cured by curing source 40. Curing source 40 is preferably a heater similar to curing source 37. Bonding occurs between substrate 22 and silicone rubber coating 24 as curing is completed, forming composite top sheet 16. Top sheet 16 is thereafter discharged from drum 36 at discharge idler roll 42.

In a particularly preferred embodiment of the present invention, heaters 37 and 40 heat the silicone rubber 34 and 24 between 100° F. and 200° F., respectively, when drum 36 has a surface speed between 50 and 750 FPM. Drum 36 is preferably 6 inches to 36 inches in diameter and has an outer surface made of stainless steel or chrome plating.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A composite material for controlling oxygen flux into a thermal cell comprising:
   a) a bottom sheet formed to have a pocket, said bottom sheet being impermeable to oxygen;
   b) a plurality of particles placed in said pocket, said plurality of particles reacting exothermally when exposed to oxygen; and
   c) a top sheet sealed to said bottom sheet at a flange around said pocket to enclose said plurality of particles such that said particles cannot fall out of said pocket, said top sheet having a substrate which is highly permeable to oxygen, said substrate being coated with an oxygen permeable silicone based elastomer to a thickness which regulates an oxygen flux into said pocket when said top sheet is exposed to oxygen, wherein said oxygen flux into said pocket is about $1.5 \times 10^5$ cm$^3$/100 in.$^2$/day to about $3.5 \times 10^5$ cm$^3$/ 100 in.$^2$/day.

2. The composite material of claim 1 further comprising:
   d) means for preventing exposure of said top sheet to oxygen until said thermal cell is intended to be used.

3. The composite material of claim 2 wherein the means for preventing exposure comprises an oxygen impermeable barrier film bonded to said top sheet by pressure sensitive adhesive, said oxygen impermeable barrier film being peelable from said oxygen permeable silicone based elastomer.

4. The composite material of claim 2 wherein the means for preventing exposure comprises an oxygen impermeable pouch into which a body warmer having said thermal cell is placed for storage.

5. The composite material of claim 1 wherein said oxygen flux into said pocket is about $1.75 \times 10^5$ cm$^3$/100 in.$^2$/day.

6. The composite material of claim 1 wherein said plurality of particles comprises a reactive iron mixture, said mixture including activated carbon, water, and salts to increase an exothermic reaction rate when said mixture is exposed to oxygen.

7. The composite material of claim 1 wherein said substrate comprises a nonwoven having openings of at least 2 microns, and said silicone based elastomer comprises poly (dimethyl siloxane) printed onto said substrate at a thickness of about 0.0001 inches.

8. A composite material for controlling oxygen flux into a thermal cell comprising:
   a) a bottom sheet formed to have a pocket, said bottom sheet being impermeable to oxygen;
   b) a plurality of particles placed in said pocket, said plurality of particles including a reactive iron mixture, said mixture including activated carbon, water, and salts to increase an exothermic reaction rate when said mixture is exposed to oxygen; and
   c) a top sheet sealed to said bottom sheet at a flange of said pocket to enclose said plurality of particles such that said particles cannot fall out of said pocket, said top sheet including a nonwoven having openings of at least 2 microns, which is highly permeable to oxygen, said nonwoven having an outer surface, said outer surface being printed with a poly (dimethyl siloxane) to a thickness of about 0.0001 inches to regulate an oxygen flux into said pocket when said top sheet is exposed to oxygen.

9. The composite material of claim 8 wherein said oxygen flux into said pocket is about $1.75 \times 10^5$ cm$^3$/100 in.$^2$/day.

10. The composite material of claim 8 further comprising:
    d) means for preventing exposure of said top sheet to oxygen until said thermal cell is intended to be used.

11. The composite material of claim 10 wherein the means for preventing exposure comprises an oxygen impermeable barrier film bonded to said top sheet by pressure sensitive adhesive, said oxygen impermeable barrier film being peelable from said poly (dimethyl siloxane).

12. The composite material of claim 10 wherein the means for preventing exposure comprises an oxygen impermeable pouch into which a body warmer having said thermal cell is placed for storage.

13. A composite material for controlling oxygen flux therethrough comprising:
    a) an oxygen porous substrate; and
    b) an oxygen permeable silicone based elastomer coated onto said oxygen porous substrate to a thickness which regulates an oxygen flux ranging from about $1.5 \times 10^5$ cm$^3$/100 in.$^2$/day to about $3.5 \times 10^5$ cm$^3$/100 in.$^2$/day through said composite material.

14. The composite material of claim 13 further comprising: an oxygen impermeable barrier film bonded to said oxygen permeable silicone based elastomer by pressure sensitive adhesive, said oxygen impermeable barrier film being peelable from said oxygen permeable silicone based elastomer.

* * * * *

UNITED STATES PATENT AND TRADEMARK OFFICE
CERTIFICATE OF CORRECTION

PATENT NO. : 5,718,955

DATED : February 17, 1998

INVENTOR(S) : McGuire et al.

It is certified that error appears in the above-identified patent and that said Letters Patent is hereby corrected as shown below:

On title page, item [54] and col. 1, lines 1-2,

"Composite for Controlling Oxygen Flux Into Thermal Cells" should read --Composite Film for Controlling Oxygen Flux Into Thermal Cells--.

Column 6, line 19, "oxygen." should read --oxygen, wherein said oxygen flux into said pocket is about $1.5 \times 10^5$ $cm^3/100$ $in.^2/day$ to about $3.5 \times 10^5$ $cm^3/100$ $in.^2/day$.--.

Column 6, line 41, "material." should read --material, wherein said substrate comprises a nonwoven having openings of at least 2 microns, and said silicone based elastomer comprises poly (dimethyl siloxane) printed onto said substrate at a thickness of about 0.0001 inches.--.

Signed and Sealed this

Sixteenth Day of June, 1998

Attest:

BRUCE LEHMAN

*Attesting Officer*      Commissioner of Patents and Trademarks